(12) United States Patent
Kahlman et al.

(10) Patent No.: US 9,177,377 B2
(45) Date of Patent: Nov. 3, 2015

(54) OPTIMIZED DETECTOR READOUT FOR BIOSENSOR

(71) Applicant: KONINKLIJKE PHILIPS N.V., Eindhoven (NL)

(72) Inventors: Josephus Arnoldus Henricus Maria Kahlman, Tilburg (NL); Bart Michiels, Turnout (BE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/580,293

(22) Filed: Dec. 23, 2014

(65) Prior Publication Data

US 2015/0110371 A1    Apr. 23, 2015

Related U.S. Application Data

(62) Division of application No. 12/810,531, filed as application No. PCT/IB2008/055402 on Dec. 18, 2008, now Pat. No. 8,945,472.

(30) Foreign Application Priority Data

Jan. 4, 2008   (EP) .................................. 08100087

(51) Int. Cl.
*G01N 21/00*     (2006.01)
*G06T 7/00*      (2006.01)
(Continued)

(52) U.S. Cl.
CPC ............ *G06T 7/0012* (2013.01); *G01N 21/274* (2013.01); *G01N 21/552* (2013.01); *A61M 2205/3306* (2013.01); *G01J 1/44* (2013.01); *G01J 1/46* (2013.01); *G01N 15/0205* (2013.01); *G01N 15/0211* (2013.01);
(Continued)

(58) Field of Classification Search
CPC .......... G01N 15/0205; G01N 15/0211; G01N 21/65; G01J 1/46; G01J 1/44; A61M 2205/3306; G09G 2300/0443; G09G 2300/0809; G09G 2340/0435; G09G 3/3233
See application file for complete search history.

(56) References Cited

U.S. PATENT DOCUMENTS 3,787,620 A    1/1974   Pieters et al.
4,844,613 A    7/1989   Batchelder et al.
(Continued)

FOREIGN PATENT DOCUMENTS

EP    1394532 A2    3/2004
EP    1703464 A1    9/2006
(Continued)

OTHER PUBLICATIONS

Tao et al: "High Resolution Surface Plasmon Resonance Spectroscopy"; Review of Scientific Instruments, Dec. 1999, vol. 70, No. 12, pp. 4656-4660.

*Primary Examiner* — Dennis M White

(57) ABSTRACT

The present invention provides a biosensor system comprising a light source, a cartridge adapted to be illuminated by said light source, a light detector adapted for detecting a signal originating from the cartridge, an illumination control means adapted to vary the illumination of the cartridge between at least two different states, a means for generating a first oscillation with a first frequency, and a means for generating a second oscillation with a second frequency, wherein the frame rate of the light detector is triggered by the first oscillation and the illumination control means is triggered by the second oscillation.

4 Claims, 3 Drawing Sheets

(51) Int. Cl.
*G01N 21/27* (2006.01)
*G01N 21/552* (2014.01)
*G09G 3/32* (2006.01)
*G01J 1/46* (2006.01)
*G01N 21/65* (2006.01)
*G01J 1/44* (2006.01)
*G01N 15/02* (2006.01)

(52) U.S. Cl.
CPC ....... *G01N 21/65* (2013.01); *G01N 2201/0691* (2013.01); *G06T 2207/10004* (2013.01); *G06T 2207/10152* (2013.01); *G06T 2207/30004* (2013.01); *G09G 3/3233* (2013.01); *G09G 2300/0443* (2013.01); *G09G 2300/0809* (2013.01); *G09G 2340/0435* (2013.01); *Y10S 435/808* (2013.01); *Y10S 436/805* (2013.01)

(56) References Cited

U.S. PATENT DOCUMENTS

| | | | |
|---|---|---|---|
| 5,428,558 A * | 6/1995 | Cahill et al. | ............... 356/319 |
| 5,468,620 A | 11/1995 | Molloy et al. | |
| 6,584,217 B1 | 6/2003 | Lawless et al. | |
| 2002/0033989 A1 | 3/2002 | Fisher et al. | |
| 2006/0012795 A1 | 1/2006 | Niemax et al. | |
| 2006/0019265 A1 | 1/2006 | Song et al. | |
| 2006/0142947 A1 * | 6/2006 | Robrish et al. | ............... 702/19 |

FOREIGN PATENT DOCUMENTS

| | | |
|---|---|---|
| WO | 9940536 A1 | 8/1999 |
| WO | 2008155723 A1 | 12/2008 |

* cited by examiner

OPTIMIZED DETECTOR READOUT FOR BIOSENSOR

CROSS-REFERENCE TO PRIOR APPLICATIONS

This application is a Divisional application of U.S. application Ser. No. 12/810,531, filed on Sep. 16, 2010, which is the U.S. National Phase Application of International No. PCT/IB2008/055402, filed on Dec. 18, 2008 and claims the benefit of European Patent Application No. 08100087.9, filed on Jan. 4, 2008. These applications are hereby incorporated by reference herein.

FIELD OF THE INVENTION

The invention relates to a method of improved readout of an optical detector of biosensors and to a system to be used for said method.

BACKGROUND OF THE INVENTION

The demand for biosensors is increasingly growing these days. Usually, biosensors allow for the detection of a given specific molecule within an analyte, wherein the amount of said molecule is typically small. Therefore, target particles, for example super-paramagnetic label beads, are used which bind to a specific binding site or spot only, if the molecule to be detected is present within the analyte. One known technique to detect these label particles bound to the binding spots is FTIR. Therein, light is coupled into the sample at an angle of total internal reflection. If no particles are present close to the sample surface, the light is completely reflected. If, however, the label particles are bound to said surface, the condition of total internal reflection is violated, a portion of the light is scattered into the sample and thus the amount of light reflected by the surface is decreased. By measuring the intensity of the reflected light with an optical detector, it is possible to estimate the amount of particles bound to the surface.

Typically, a photodiode is used as an optical detector. However, a detection by a (CCD) camera or any other multi-pixel system is much more efficient, since a camera allows for the parallel detection of various binding sites or spots. The disadvantage of the use of a camera, though, is that accurate measurements of the intensity of the binding spots is difficult due to gain —and offset errors in the read-out system.

SUMMARY OF THE INVENTION

It is therefore an object of the present invention to provide an improved optical detector readout for biosensors. This object is achieved with the features of the claims.

The present invention is based on the idea to modulate the amplitude of the light coupled into the sample and to simultaneously detect the light reflected by the sample surface or originating from the sample. Thus, the relative darkening of the binding spot(s) can be measured accurately.

The present invention provides a biosensor system comprising a light source, a cartridge adapted to be illuminated by said light source, a light detector adapted for detecting a signal originating from the cartridge, an illumination control means adapted to vary the illumination of the cartridge between at least two different states, a means for generating a first oscillation with a first frequency, and a means for generating a second oscillation with a second frequency, wherein the frame rate of the light detector is determined, e.g. triggered, by the first oscillation and the illumination control means is determined, e.g. triggered, by the second oscillation.

The frame rate of the detector being triggered by the first oscillation does not imply that the integration time of the detector is determined by said oscillation as well. The integration time may be either determined by the detector or its control or by the waveform of said first oscillation. The same holds true for the triggering of the illumination control means by the second oscillation.

Therein the second frequency is preferably equal to one half of the first frequency. Thus, the cartridge experiences two different illumination states, for example, one illumination state, which is substantially dark, and a second illumination state, which is substantially bright. Due to the triggering of the light detector by the first oscillation alternate images are taken from the dark and the bright state. This allows for an improved image analysis, since said dark state contains information regarding noise, background, inhomogeneous illumination and the like.

However, other frequency ratios for dark versus bright frames than 1:1 are possible as well. This, in particular, depends on the band width of the disturbances, i.e. the noise. A ratio of 1:1 combines maximum reduction band-width with maximum number of bright frames. Yet, if only a slowly varying dark current has to be suppressed, this ratio may be, e.g., 1:10. In that case, most of the frames are bright allowing for more information to be gathered from the binding spots themselves.

The light detector may, in particular, comprise a video or CCD camera. In that case, the (electronic) shutter of the camera may be used alternatively to modulate the light amplitude between two values instead of modulating the light source itself However, this does not allow for background light induced before the camera sensor to be suppressed. But other detectors are conceivable as well, for instance discrete photo-diodes or any suitable multi-pixel system.

The system may further comprise a video processing software for analyzing the output of the video or CCD camera and optics for projecting the light reflected by or originating from the cartridge onto the light detector or camera.

The present invention also relates to a method of detecting relative darkening at a binding spot of a biosensor cartridge. Said method comprises the steps of taking a first image of the binding spot and its surrounding at a first illumination and analyzing the intensity of said first image at the binding spot $I_1(A)$ and at its surrounding $I_1(B)$. Then a second image of the binding spot and its surrounding at a second illumination is taken and the intensity of said second image at the binding spot $I_2(A)$ and at its surrounding $I_2(B)$ is analyzed. Finally, the relative darkening of the binding spot is calculated. Therein, the second illumination has a higher intensity than the first illumination. Optionally, the method further comprises the step of identifying the binding spot.

Preferably, the relative darkening D of the binding spot is calculated by $D=(I_2(A)-I_1(A))/(I_2(B)-I_1(B))$. But other ways to calculate the relative darkening are possible as well. For example, the steps of analyzing the intensity of the first and second image may be performed pixel-wise.

Of course, neither the biosensor system nor the method of detection is limited to frame-by-frame illumination modulation. Different parts of the frame may be illuminated differently. It is, for example, conceivable that the detector progressively scans pixels or regions like, e.g., horizontal stripes of the image.

The described method may be implemented into different known techniques to perform bio-sensing. For instance, the amount of label particles close to the sensor surface may be measured by frustrated total internal reflection (FTIR). However, the method according to the present invention is not limited to any specific sensing technique or sensor. The sensor can be any suitable sensor to detect the presence of particles on or near to a sensor surface, e.g. by imaging, fluorescence, chemi-luminescence, absorption, scattering, evanescent field techniques, surface plasmon resonance, Raman, etc.

These and other aspects of the invention will be apparent from and elucidated with reference to the embodiment(s) described hereinafter.

DETAILED DESCRIPTION OF EMBODIMENTS

Figure 1:
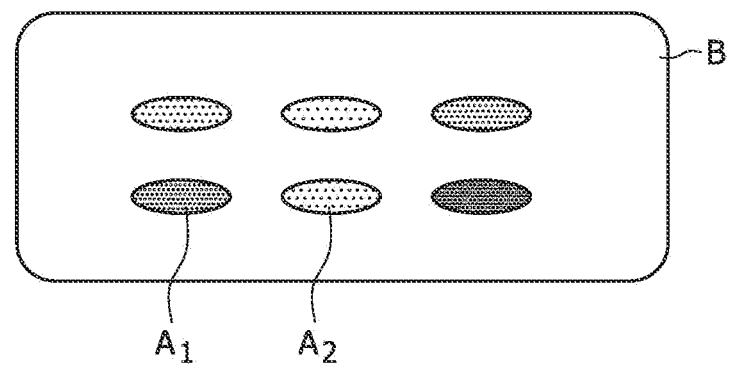
FIG. 1 schematically shows a camera picture obtained by FTIR.

FIG. 1 schematically shows a camera picture obtained by FTIR. This picture is obtained by (predominantly) homogeneous illumination of the FTIR surface of a cartridge and projection of the reflected light via an optical system on a (CCD) camera. Therein, six binding sites or spots $A_1$, $A_2$ can be identified in a region B with a certain background illumination or noise level. The brightness of the binding sites depends on the amount of label particles bound to these sites: The more label particles are bound the more light is scattered at the respective region causing a decrease of the reflected light. Thus, a dark binding site indicates a large amount of bound label particles. The relative darkening D of a binding spot compared to the surrounding area is a measure for the number of bindings and accordingly for the amount of a specific molecule within the sample liquid.

However, said relative darkening cannot be measured accurately because of gain- and offset errors in the read-out system. This is caused by unknown optical gain in the optical light path, the level of illumination, gain parameters in the camera (exposure time, shutter, active pixels etc.). Further negative effects are spurious background light and dark current in the camera.

In a typical FTIR geometry, small signal changes from the label particles or beads are detected on a relatively large optical base line signal. Said optical base line signal originates from the large reflection from the surface of the binding surface. Due to this large optical base line signal, gain variations originating from temperature effects (drift) in the sensor, in the signal processing and optical light path will introduce large variations in the detected signal, which limits the achievable accuracy and detection limit of the biosensor. This is especially a problem during relatively long-time measurements for low target-concentrations.

Moreover, demands on the dynamic range of the detection electronics are quite severe for high-sensitivity applications. Furthermore, spurious light sources from ambient and lighting may disturb the measurement.

Figure 2:
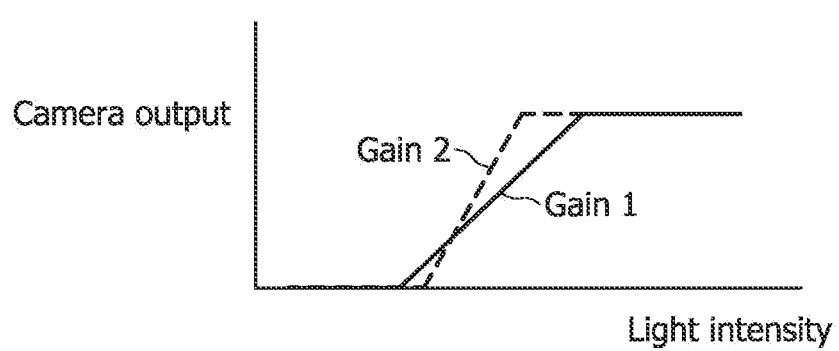
FIG. 2 illustrates a camera response for two different gains.

The camera response, which is the output per pixel versus the applied light intensity, can vary between pixels due to manufacturing tolerances. Furthermore the gain depends on many parameters like exposure time, shutter setting, selected pixels (black-white or color) and is not well defined. FIG. 2 illustrates two different responses of a typical pixel due to different gains. The dynamic range is generally determined by the resolution, e.g. 8 bits.

Figure 3:
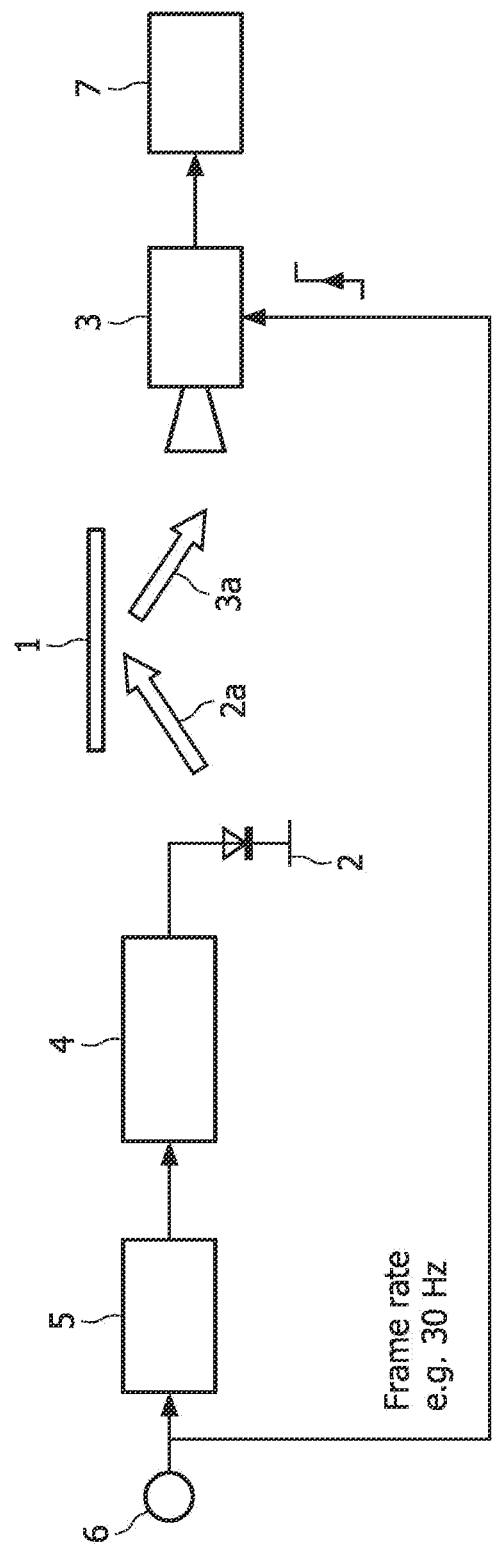
FIG. 3 schematically shows an embodiment of an FTIR system according to the present invention.

FIG. 3 schematically shows an embodiment of an FTIR system according to the present invention. An FTIR cartridge 1 is illuminated by a light source 2. This may be, e.g., a laser or LED. The incoming light 2a fulfils the condition of total internal reflection and is reflected at a sensor surface of the cartridge 1. The reflected light 3a is detected at a camera 3, which may be, e.g., a CCD camera. The incoming light 2a generates an evanescent wave within the cartridge 1. A portion of said wave is scattered if an optical inhomogeneity, e.g., a label particle, is present close to the surface of the cartridge. Accordingly, the intensity of the reflected light 3a detected at camera 3 is varied.

According to the invention, the light source 2 is controlled by an illumination light control means 4. In particular, the intensity of the light emitted by the light source 2 can be controlled by control means 4.

The system further comprises an oscillator 6, which generates a first oscillation of a first frequency, e.g., 30 Hz. The frame rate of the camera 3 is determined by said first oscillation. A divider 5 divides the first frequency by a factor, preferably 2, in order to generate a second oscillation with a second frequency. In the exemplary case of the first frequency being 30 Hz and the factor being 2, the second frequency will be 15 Hz. Said second oscillation triggers the illumination light control means 4.

Thus, the intensity of the illumination is varied with a second frequency, e.g. 15 Hz, whereas the frame rate of the camera equals a first frequency, e.g., 30 Hz. Accordingly, bright and dark pictures of the reflected light 3a are taken in an alternating manner. These bright and dark pictures are then analyzed by a software 7, e.g. LabView or any other suitable software.

Alternatively the (electronic) shutter of the camera 3 may be used to modulate the light amplitude between two values instead of modulating the light source 2 itself. As already mentioned above, this does not allow for a reduction of background light.

Figure 4A:
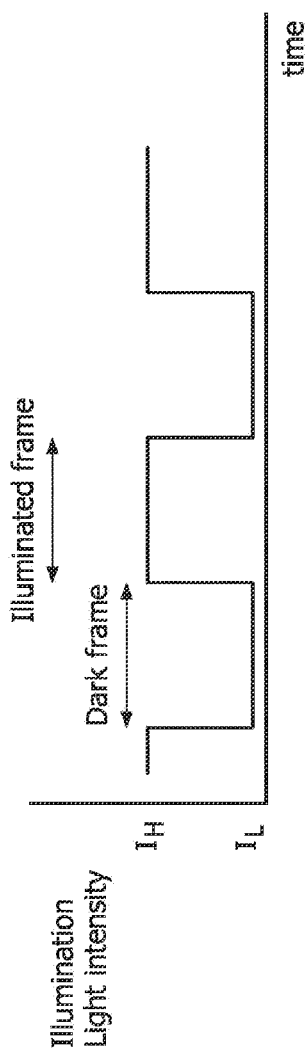
FIG. 4a depicts a diagram showing the illumination light intensity versus time.
Figure 4B:
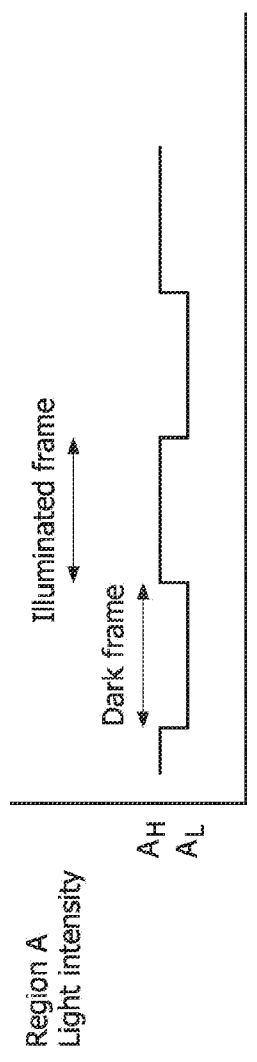
FIG. 4b depicts a diagram showing the light intensity of region A versus time.
Figure 4C:
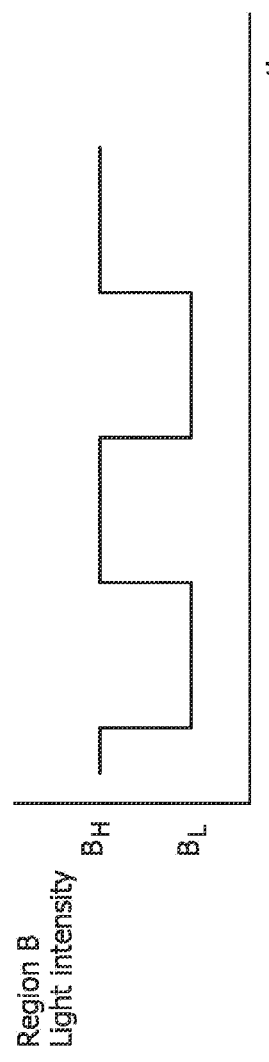
FIG. 4c depicts a diagram showing the light intensity of region B versus time.

FIG. 4a depicts a diagram showing the varying intensity of the illumination light 2a versus time. As described above, a dark frame with a low intensity $I_L$ (which may be zero) is followed by a bright frame with a high intensity $I_H$. Accordingly, the background intensity of region B (cf. FIG. 1) of the pictures taken by camera 3 will vary in a corresponding pattern as shown in FIG. 4c: If the cartridge is illuminated with low intensity the background intensity $B_L$ will be low as well. If the cartridge is illuminated with high intensity the background intensity $B_H$ will be increased as well.

The same holds true for the intensity of a binding spot A (cf. FIG. 1). The alternating intensities $A_L$ and $A_H$ of a specific binding spot or site are shown in FIG. 4b. Of course, the absolute values of these intensities will depend on the specific binding spot as is apparent from FIG. 1. Nevertheless, the pattern of varying intensity over time is similar for all binding spots.

Said bright and dark frames are transferred to the video processing software 7, which makes interfacing stable and robust, since the camera and software are "slave" of the illumination sequence and there is no need for interface control loops or the like.

The relative average darkening D of the binding spots can easily be calculated according to $$D = \frac{A_H - A_L}{A_{H_{t=0}} - A_{L_{t=0}}} \cdot \frac{B_{H_{t=0}} - B_{L_{t=0}}}{B_H - B_L} \cdot 100[\%].$$

At the start of the assay the cartridge is "white", hence the average intensities at t=0 (i.e., the beginning of the assay) fulfil the equation $A_{H_{t=0}} - A_{L_{t=0}} = B_{H_{t=0}} - B_{L_{t=0}}$. As a result the relative darkening D of the binding spots reduces to $$D = \frac{A_H - A_L}{B_H - B_L} \cdot 100[\%],$$

where $B_L$ and $B_H$ are the averaged light values across the total background area B.

This method, however, gives no information of the binding distribution within a binding spot as just the average relative darkening is calculated for each binding spot. Therefore, an improved processing is suggested to calculate the relative darkening per pixel.

When the binding distribution within a binding-spot has to be assessed, there is a need for a gain—and offset corrected image. Hence, for every pixel P in the image the relative darkening $D_P$ is calculated referenced to the white area according to:

$$D_P = \frac{P_H - P_L}{P_{H_{t=0}} - P_{L_{t=0}}} \cdot \frac{B_{H_{t=0}} - B_{L_{t=0}}}{B_H - B_L} \cdot 100[\%].$$

In contrast to the method described above, $P_{H_{t=0}} - P_{L_{t=0}} \neq B_{H_{t=0}} - B_{L_{t=0}}$, because the actual pixel values may deviate from the average.

Obviously, the average relative darkening of the binding spots A is:

$$D = \frac{\sum_{i=1}^{n} D_{P_i}}{n},$$

which is more accurate in case of non-uniform offset light compared to the value obtained with the method described above.

The system of the present invention provides several advantages: No forward sense or monitor diode needed, as is typically the case for FTIR. The achieved results are gain independent. Spurious background light and camera dark-current are suppressed. And the interfacing to software of the system is easy and robust.

Of course, the method described in the present invention, although described with respect to an FTIR sensor, is not restricted to FTIR. The sensor can be any suitable sensor to detect the presence of particles on or near to a sensor surface, based on any property of the particles, e.g. by reflective or transmissive imaging, fluorescence, chemiluminescence, absorption, scattering, evanescent field techniques, surface plasmon resonance, Raman, etc.

The method according to the present invention can be used with several biochemical assay types, e.g. binding/unbinding assay, sandwich assay, competition assay, displacement assay, enzymatic assay, etc. The methods of this invention are suited for sensor multiplexing (i.e. the parallel use of different sensors and sensor surfaces), label multiplexing (i.e. the parallel use of different types of labels) and chamber multiplexing (i.e. the parallel use of different reaction chambers). The methods described in the present invention can be used as rapid, robust, and easy to use point-of-care biosensors for small sample volumes. The reaction chamber can be a disposable item to be used with a compact reader, containing the one or more magnetic field generating means and one or more detection means. Also, the methods of the present invention can be used in automated high-throughput testing. In this case, the reaction chamber is e.g. a well plate or cuvette, fitting into an automated instrument.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or an does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A method of detecting relative darkening at a binding spot of a biosensor cartridge having a reflective surface and label particles causing an optical inhomogeneity, said method comprising the acts of:

illuminating the cartridge by incoming light from a light source for generating an evanescent wave having a portion scattered due to presence of the label particles;

taking a first image of the binding spot and its surrounding at a first illumination of the cartridge by the incoming light at a frame rate determined by a first oscillation having a first frequency;

taking a second image of the binding spot and its surrounding at a second illumination of the cartridge by the incoming light at a frame rate determined by a second oscillation having a second frequency derived by dividing the first oscillation having the first frequency;

analyzing the intensity of said first and second images at the binding spot and at its surrounding; and calculating the relative darkening of the binding spot, wherein the second illumination has a higher intensity than the first illumination.

2. The method according to claim 1, wherein the relative darkening of the binding spot is calculated by $D=(I_2(A)-I_1(A))/(I_2(B)-I_1(B))$ where $I_1(A)$ is the intensity of the first image at the binding spot;

$I_1(B)$ is the intensity of the first image at its surrounding;
   $I_2(A)$;

$I_2(A)$ is the intensity of the second image at the binding spot; and $I_2(B)$ is the intensity of the second image at its surrounding.

3. The method according to claim 1, further comprising an act of identifying the binding spot.

4. The method according to claim 1, wherein the analyzing and calculating acts are performed pixel-wise.

* * * * *